United States Patent [19]

Allinson

[11] 4,262,663

[45] Apr. 21, 1981

[54] PENILE SUPPORT

[76] Inventor: Francis W. Allinson, 53 W. Lewis, Phoenix, Ariz. 85003

[21] Appl. No.: 110,085

[22] Filed: Jan. 7, 1980

Related U.S. Application Data

[63] Continuation-in-part of Ser. No. 82,958, Oct. 9, 1978, which is a continuation-in-part of Ser. No. 12,836, Jan. 16, 1979, which is a continuation-in-part of Ser. No. 970,490, Dec. 18, 1978, abandoned.

[51] Int. Cl.³ .................................................. A61F 5/00
[52] U.S. Cl. ......................................................... 128/79
[58] Field of Search ............................................. 128/79

[56] References Cited

U.S. PATENT DOCUMENTS

| | | | |
|---|---|---|---|
| 764,801 | 7/1904 | Emerson | 128/79 |
| 3,920,007 | 11/1975 | Line | 128/79 |

FOREIGN PATENT DOCUMENTS

| | | | |
|---|---|---|---|
| 831874 | 2/1952 | Fed. Rep. of Germany | 128/79 |
| 711544 | 6/1931 | France | 128/79 |
| 1144083 | 3/1969 | United Kingdom | 128/79 |
| 589978 | 1/1974 | U.S.S.R. | 128/79 |

Primary Examiner—John D. Yasko

[57] ABSTRACT

A malleable clip-on self-retaining outline penile support used to make the sexual act possible in the case of male weakness. The device consists of a pliable distal head piece, joined by two malleable ventral longitudinal supports, which may or may not be covered by pliable tubing, and which can be made to conform to the curve of the overlying penis, and which unite proximally with a generally looped-shaped proximal portion; an additional proximal ventral loop can be added. The malleability of the proximal looped portion enables adjustment transversely of the proximal ends of the longitudinal supports and of itself to be made; this proximal gripping force is also transmitted distally to the head piece. A malleable angle at the junction of the proximal loop and the proximal end of each longitudinal support enables adjustment in length of the penile support to be made. The head piece is interchangeable. A wide thin elastic member can be used for additional fixation. An alternate embodiment with an additional proximal ventral fixation loop is included.

9 Claims, 11 Drawing Figures

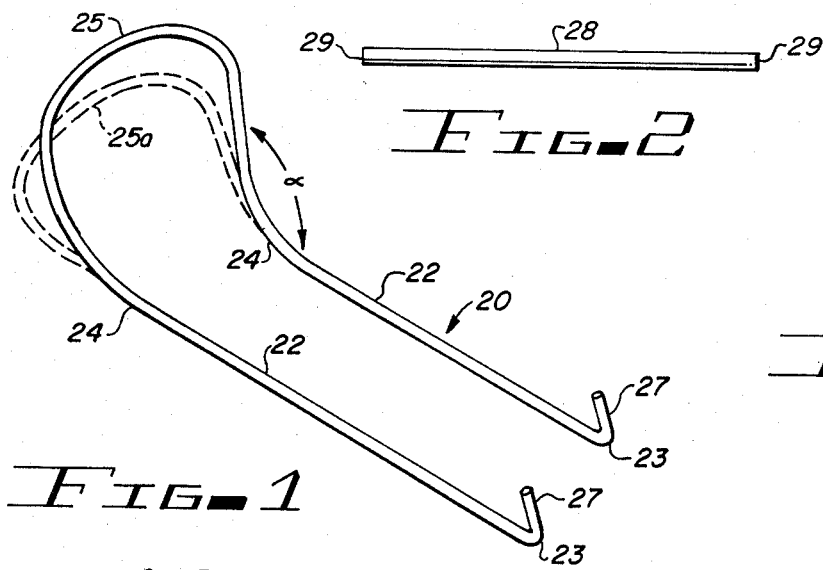

PENILE SUPPORT

This is a continuation-in-part of my patent application, Ser. No. 082,958 filed Oct. 9, 1978, which in turn is a continuation-in-part of application Ser. No. 12,836, filed Jan. 16, 1979, which was a continuation-in-part of my original patent application, Ser. No. 970,490, filed Dec. 18, 1978, now abandoned.

PRIOR ART STATEMENT

The flattened metal and wire splint described by Loewenstein of London, England in 1947 and, at that time, made by Down Bros., British patent unknown. This is a multiple hinged and multiple jointed splint with a proximal elastic accumulator attached to projecting ventral arms which transmit contracting force along the ventral supports to the distal loop.

U.S. Pat. No. 1,153,072 discloses a sleevelike body having longitudinally disposed slits for flexibility. This splint completely encircles the penis and is made from rubber to render the splint flexible and resilient.

U.S. Pat. No. 3,131,691 describes a proximal and distal web with a cradle on the undersurface and a strut on the opposite surface. The cradle has a body of soft surgical rubber. Embedded within is a concave steel reinforcement.

U.S. Pat. No. 1,585,861 discloses an elongated member made of a sufficiently rigid material to meet all requirements. Concave in cross-section extending less than a semi-circle and lies mostly ventrally and is held in place by elastic bands. The sides are firmly united to each other both distally and proximally.

U.S. Pat. No. 844,798 discloses stiffening members extending on opposite sides of the organ. Elastic weblike connection distally to encircle the corona. An elastic jacket encircles the device to keep it in position.

U.S. Pat. No. 3,401,687 teaches a longitudinally split tube made of a flexible material with a light spring action. This is completely surrounded by an elastic cover.

U.S. Pat. No. 1,216,099 discloses the support which is a split sleeve of rubber and it encloses the organ. Each side of the splint has a series of perforated lugs and an engagement rod for fixation.

U.S. Pat. No. 3,495,588 discloses a surgical splint comprising a unitary flexible and rigid tubular shank open at both ends to aid in extraction during copulation.

U.S. Pat. No. 3,982,530 discloses at least four supporting ribs extending proximally from the distal base. The male organ is completely encased. It is made from a thin relatively rigid material such as a plastic or metal sheet with a plastic coating.

U.S. Pat. No. 3,820,533 discloses an inflatable ring at the base for compression and a tubular sleeve portion.

U.S. Pat. No. 1,346,463 discloses a pair of elongated thin flat metallic bars joined proximally by a spring yoke and distally by a spring ring; the splint is formed of a spring metal or equivalent material. In the main splint there are several sustaining elements proximally. In the modified splint, the distal loop is hinged.

Pat. No. 831874 (German) 1949 consists of connecting rods and rings made out of 1 mm steel wire covered by pressed rubber or rubber hose. With the special feature that the ring that surrounds the glans penis is positioned obliquely towards the back.

Pat. No. 102097 (German) 1925 consists of a double walled rubber cartridge, with a thinner inner wall than outer. There are inlays at intervals which press against the sides of the shaft of the penis. The lumen of this cartridge can be distended with air to produce stiffness and aid in erection.

Pat. No. 368352 (German) 1923 consists of a cylindrical appliance with cut outs giving rise to strips made of hard rubber or steel or similar substance, which end in a cap connected with elastic bands to side strips of cylinder.

It is not believed that any of the devices described in the foregoing patents are satisfactory for the following reasons:

The wire splint by Loewenstein has multiple hinges, it is rigid and clumsy, and the distal loop conforms in no way to the coronal sulcus of the penis.

U.S. Pat. No. 1,153,072 discloses a device which completely encloses the shaft of the penis and appears difficult to apply. It is made from rubber.

U.S. Pat. No. 3,131,691 shows a ventral cradle and a dorsal strut. There is insufficient exposure of the shaft of the penis and the splint would be difficult to apply due to the presence of proximal and distal webs. There is flexibility but not malleability of the device.

U.S. Pat. No. 1,585,861 discloses the importance of its use for nonsexual purposes as opposed to sexual purposes is stressed, and when used for the latter purpose, it is inadequate for the following reasons: The ventral longitudinal support is a single unit with a longitudinal slit in the center of its long axis, it is semi-rigid and nonadjustable laterally, its proximal band, and more especially, the distal band, is inadequate for fixation with this single unsplit ventral support which would be unable to grip the sides of the frenum for fixation.

U.S. Pat. No. 844,798, by Hawley in 1907, discloses two lateral supports which are too wide and would thus prevent adequate contact between the penis and vagina. The tight rubber opening distally could make it difficult to insert the glans penis through the opening. The splint is covered.

U.S. Pat. No. 3,401,687 discloses a plastic support completely encircling the shaft of the penis with resulting poor contact between the penis and the vagina. An elastic cover is used, further limiting contact.

U.S. Pat. No. 1,216,099 discloses a split sleeve of rubber joined by lugs. It is altogether too complex and entirely surrounds the shaft of the penis.

U.S. Pat. No. 3,495,588 discloses a removable tubular shank enclosing the ventral and lateral aspects of the penis. Too much of the shaft of the penis is covered by a rigid material.

U.S. Pat. No. 3,982,530 discloses that the penis is completely enclosed and the glans penis does not project beyond the end of the splint and therefore does not make adequate contact with the vagina. Formed from a thin relatively rigid material such as a plastic or metal sheet with a plastic coating.

U.S. Pat. No. 3,820,533 discloses a too complicated device with an inflatable ring at the base. Is made of relatively rigid or flexible plastic material. This splint could produce trauma to the vagina.

U.S. Pat. No. 1,346,463, by Renois in 1920, discloses two splints, the main splint and the modified splint. In the main splint there are several sustaining elements proximally and these could well irritate the vaginal outlet during use, especially dorsally where these sustaining elements approach each other at a sharp angle. In the modified splint, the distal spring ring is hinged. This could lead to inadequate fixation. As the splint is formed of spring metal or equivalent material, there are no means of lengthening or shortening the support; nor is the head piece interchangeable or flexible.

Pat. No. 831874 (German) 1949 is completely made of 1 mm steel wire with no mention of malleability. Under these conditions the whole support could be too rigid if the connecting rods are sufficiently strong to resist bending during use or too weak if the distal ring was sufficiently malleable to conform to the coronal sulcus of the penis with comfort and ease. Severe damage to the vagina could occur during removal should slipping forwards of the splint occur during use due to the unyielding backwards projection of the distal ring.

Pat. No. 102097 (Germany) 1925 is made of a double-walled rubber cartridge with inlays to aid in erection completely surrounding the shaft of the penis but leaving the glands exposed. Once applied it can be inflated by air. This is a clumsy device and completely surrounds the shaft of the penis, thus lessening contact between penis and vagina.

Pat. No. 368352 (German) 1923 has multiple strips surrounding the body of the penis which extend distally to cover most of the head of the penis. All this precludes adequate contact between the penis and the vagina.

SUMMARY OF THE INVENTION

A malleable clip-on self-retaining outline penile support, used to make the sexual act possible in the case of male weakness. The device consists of a pliable interchangeable head piece joined by two malleable longitudinal supports which join proximally a looped-shaped proximal portion which extends proximally and dorsally to surround the sides and dorsum of the penis, and in so doing, the proximal portion of the support will come to rest in front of the synphysis pubis when in use. The distal portion of each longitudinal support is angled dorsally proximally and slightly laterally and receive the ends of the tubular pliable part of the head piece and contributes to the less pliable portion. Malleability transversely of the proximal part of this looped-shaped proximal portion permits adjustment of the proximal ends and the whole length and distal ends of the longitudinal supports, and a malleable angle towards the proximal end of each longitudinal support at the junction with the proximal looped-portion of the support enables the length of the penile support to be varied. The pliable dorsal portion of the head piece permits acute forward flexion of this dorsal portion to occur for safe removal should slipping forwards of the support occur during use. The more resistant ventral portion of the head piece is essential for adequate fixation. Additional fixation distally is achieved by the use of a wide thin elastic member. An alternative embodiment shows the proximal portion of each slightly elongated longitudinal support looped ventrally and inwards to join the now proximally concave curved looped-shaped portion of the support.

BRIEF DESCRIPTION OF THE DRAWINGS

The foregoing and further and more specific objects and advantages of the instant invention will become readily apparent to those skilled in the art from the following detailed description of preferred embodiments therefor taken in conjunction with the drawings, in which:

FIG. 1 is a perspective view of the malleable portion of a penile support constructed in accordance with my invention.

FIG. 2 is a plan view of the pliable tubing used for forming the head piece as it would appear prior to attachment to the wire support.

FIG. 3 is a fragmentary plan view of the distal part of the support shown in FIG. 1 shown the pliable tubular part of the head piece attached to the upturned distal ends of the longitudinal supports.

FIG. 4 is a side view of an alternate embodiment of an assembled support.

FIG. 5 is a plan view of the support of FIG. 4.

FIG. 6 is a plan view of yet another and alternate embodiment of the invention.

FIG. 7 is an enlarged fragmentary perspective view of the distal end of the support of FIG. 6.

FIG. 8 is an enlarged cross-sectional view taken along the line 8—8 of FIG. 6.

FIG. 9 is an enlarged cross-sectional view taken along the line 9—9 of FIG. 6.

FIG. 10 shows an elastic member for additional fixation.

FIG. 11 is a fragmentary side view of an alternate proximal portion useful in connection with the embodiment of FIGS. 4 and 5.

Turning now to the drawings in which like reference numerals indicate corresponding elements throughout the several views, attention is first directed to FIG. 1 which shows the frame portion of the invention generally designated by the reference character 20. Frame 20 includes a pair of spaced apart elongate support elements 22, which for purposes of reference, are considered to have distal ends 23 and proximal ends 24. The support elements 22 are joined by a generally inverted U-shaped member 25 integrally joining proximal ends 24. An angularly disposed section 27 is integral with the distal end 23 of each support element 22.

Preferably, frame 20 is integrally formed of single piece of malleable material. In order to provide the desired characteristics, it is suggested that frame 20 be fabricated of soft annealed stainless steel wire of approximately 13 gauge diameter. Such material, which is manually deformable, exhibits a tensile strength of approximately 80,000 to 121,000 pounds per square inch. An alternate material is plastic, such as polyvinyl chloride, in tube or rod form of approximately 9 gauge diameter. Such materials are bendable when subjected to heat.

With reference to FIG. 2, there is seen a length of tubing 28 having open ends 29. The length of tubing 28, which is of a pliable material, is selectively variable for the purpose of fit and accommodation as will be described presently. Typically, tubing 28 is fabricated of any suitable pliable material such as polyvinyl chloride or rubber, having an outside diameter of 0.125 inches and an inside diameter chosen to receive and frictionally engage frame 20. In prototype models, tubing having a wall thickness of approximately 0.030 inches has proven to yield satisfactory functional results.

Angularly disposed sections 27 of frame 20 extend dorsalwards, i.e., slightly rearward and slightly laterally outward. It is noted that each section 27 is adjoined to the respective end 23 with a smooth rounded curve. The ends 27 of frame 20 are entered into and frictionally engaged with the open ends 29 of tubing 28, as illustrated in FIG. 3, to form tubing 28 into a curved head piece 30.

During use, support elements 22 extend along and support the overlying ventral surface of the penis with U-shaped member 25 extending upwardly therefrom over the penis. Head piece 28 extends upwardly encircling the coronal sulcus. Due to the malleability of frame 20, U-shaped member 25 is transversely deformable to produce local gripping force which is also transmitted distally by varying the spacing between support elements 22. Further, the angle alpha between U-shaped member 25 and support elements 22 is adjustably variable which effectively changes the length of the device. For purposes of illustration of the variance of angle alpha, U-shaped member 25 is shown in solid outline and an angularly displaced position shown in broken outline and designated 25a. The pliability of head piece 30 provides flexing or yieldability, especially deformability in the distal direction as indicated by the arrowed line A, to permit safe removal of the support in the event of slippage of the support during use.

FIGS. 4 and 5 illustrate an alternate embodiment of the invention which in common with the embodiment of FIG. 1 includes a frame generally designated by the reference 32 having elongate support elements 33 with distal ends 34 and proximal ends 35. An angularly disposed section 37 is integral with each distal end 34. Tubing 28 is secured at the ends 29 thereof to the sections 37 as previously described. The flexing of head piece 30 is graphically illustrated by the alternate position thereof shown in broken outline 30A.

Proximal ends 35 of support elements 33, again in general similarity to the previously described embodiment, are joined by inverted U-shaped member 38. In contrast thereto, however, a single coil loop 39 is disposed between U-shaped element 38 and each respective proximal end 35. This has the effect of raising proximal ends 35 so that they slope ventrally postero-distally. Support elements 33 also converge distally to provide increased support.

FIG. 6 illustrates yet another embodiment of the invention utilizing the frame 20 previously described. In accordance with the immediate embodiment, frame 20 is entirely encased within pliable tube 42. Portions of tube 42 are broken away to reveal the internal frame 20. Preferably, tube 42 is of slightly larger inside diameter than previously described tube 28 in order to enable it to be prolonged and uninterrupted proximally to cover the support elements 22 and the U-shaped portion 25.

As illustrated in FIG. 7, in which it is assumed that tube 42 is transparent to reveal frame 20 therewithin, tube 42 extends unsupportedly between sections 27, as further illustrated in FIG. 9, to provide flexible head piece 43. FIG. 8, a section specifically taken through a support element, is typical of the other portions of the support device.

For additional fixation of the support, an endless elastic member 45 as illustrated in FIG. 10, may be used in connection with the previously described embodiments of the invention. Preferrably, elastic member 45 is composed of a thin latex rubber which, for example, may be approximately 0.75 inches wide, having a wall thickness of approximately 0.017 inches and having a diameter of approximately 1 inch. The exact size of member 45 is optional with the user. In use, the device concurrently encircles the device of the instant invention and the penis in the area of the head piece.

Loop 39, as seen in FIGS. 4 and 5, extends through a full turn. That is, terminal portions thereof overlap. Open loop 47, as viewed in FIG. 11, as an alternate to loop 39, is also useful to connect U-shaped member 38 to support elements. Open loop 47 serves to raise ends 35 of support elements 33 and provides for adjustment of the length of the device by moving U-shaped member 38 forwardly or rearwardly in response to to bending loops 47.

Various changes and modifications to the embodiments of the device herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described and disclosed the present invention and alternately preferred embodiments thereof in such clear and concise terms as to enable those skilled in the art to understand and practice the same, the invention claimed is:

1. A penile support for engagement with the penis and for assisting in the sexual function for cases of male weakness, said support comprising:
   (a) an integrally deformable frame including
      i. a pair of spaced apart elongage support elements adapted to extend along and support the ventral surface of the penis, each said element having a distal end and a proximal end;
      ii. an inverted generally U-shaped section joining the proximal ends of said pair of support elements for extending proximally convexally over said penis; and
      iii. each of said support elements having an upwardly and proximally directed terminal section integrally connected to its distal end;
   said U-shaped section being manually deformable to vary the spacing between said support elements to conform to the diameter of the penis, said frame having means for varying the effective length of said frame; and
   (b) a pliable tubular headpiece detachably mounted on and extending between said terminal sections and adapted to fit into the coronal sulcus of the penis to removably position the corona of the penis to the distal end of said frame.

2. The support of claim 1 wherein said head piece is composed of pliable tubing having ends which grip respective said terminal sections of said pair of longitudinal support elements.

3. The support of claim 1 wherein said pliable head piece extends proximally to encase the remainder of said frame.

4. The support of claim 1 wherein said support elements are generally parallel.

5. A penile support as defined in claim 1 in which the means for varying the effective length of said frame is by varying the angular relationship between the U-shaped section and the proximal ends of said support elements.

6. A penile support as defined in claim 1 in which the means for varying the effective length of said frame is a loop between the proximal end of each support element and said U-shaped member.

7. A penile support as defined in claim 6 in which each of the loops is an open loop.

8. A penile support as defined in claim 1 which further comprises an endless elastic member adapted to encircle the frame and the penis supported by the frame substantially in the area of the headpiece.

9. A penile support as defined in claim 1 in which said support elements converge distally.

* * * * *